(12) United States Patent
Franke et al.

(10) Patent No.: US 12,391,548 B2
(45) Date of Patent: Aug. 19, 2025

(54) PROCESS FOR PRODUCING CARBON MONOXIDE-CONTAINING STREAMS

(71) Applicant: Evonik Oxeno GmbH & Co. KG, Marl (DE)

(72) Inventors: Robert Franke, Marl (DE); Peter Kreis, Dortmund (DE); Dirk Fridag, Haltern am See (DE)

(73) Assignee: Evonik Oxeno GmbH & Co. KG, Marl (DE)

( * ) Notice: Subject to any disclaimer, the term of this patent is extended or adjusted under 35 U.S.C. 154(b) by 419 days.

(21) Appl. No.: 18/067,687

(22) Filed: Dec. 16, 2022

(65) Prior Publication Data
US 2023/0192486 A1 Jun. 22, 2023

(30) Foreign Application Priority Data
Dec. 20, 2021 (EP) .................................. 21215852

(51) Int. Cl.
  *B01D 53/22* (2006.01)
  *C01B 3/50* (2006.01)
  *C07C 51/14* (2006.01)

(52) U.S. Cl.
  CPC ............ *C01B 3/501* (2013.01); *B01D 53/226* (2013.01); *C07C 51/14* (2013.01); *C01B 2203/0405* (2013.01); *C01B 2203/047* (2013.01); *C01B 2203/06* (2013.01); *C01B 2203/1258* (2013.01); *C01B 2203/146* (2013.01); *C01B 2203/148* (2013.01); *C01B 2203/1614* (2013.01); *C01B 2203/1628* (2013.01)

(58) Field of Classification Search
  CPC ..... B01D 53/228; B01D 53/226; B01D 63/00
  See application file for complete search history.

(56) References Cited

U.S. PATENT DOCUMENTS

| 6,073,461 | A | 6/2000 | McNeil et al. |
| 7,947,117 | B2 * | 5/2011 | Giroudiere .............. C01B 3/505 |
| | | | 95/55 |
| 10,471,380 | B2 * | 11/2019 | Priske .................. B01D 53/225 |
| 2003/0223931 | A1 | 12/2003 | Narayan |
| 2008/0000350 | A1 | 1/2008 | Mundschau et al. |

(Continued)

FOREIGN PATENT DOCUMENTS

| DE | 69909143 T2 | 5/2004 |
| EP | 3121184 | 1/2017 |

(Continued)

OTHER PUBLICATIONS

Extended European Search Report dated May 24, 2022, in European Patent Application No. 21215852.1, 12 pages.

*Primary Examiner* — Sharon Pregler
(74) *Attorney, Agent, or Firm* — Grüneberg and Myers PLLC

(57) ABSTRACT

A process for providing a carbon monoxide-containing stream involves a separation of synthesis gas into a hydrogen-rich gas stream and a carbon monoxide-rich gas stream containing carbon monoxide to an extent of 85% by volume or more. The separation is effected in an arrangement composed of three membrane separation stages. Prior to the performance of the membrane separation, the synthesis gas is pretreated for removal of secondary components present in the synthesis gas.

20 Claims, 1 Drawing Sheet

(56) References Cited

U.S. PATENT DOCUMENTS

| | | |
|---|---|---|
| 2015/0336046 A1 | 11/2015 | Ungerank et al. |
| 2016/0310912 A1 | 10/2016 | Ungerank et al. |
| 2017/0022235 A1 | 1/2017 | Dong et al. |
| 2020/0392057 A1* | 12/2020 | Kucmierczyk ......... C07C 29/80 |
| 2021/0179425 A1 | 6/2021 | Ott |

FOREIGN PATENT DOCUMENTS

| | | |
|---|---|---|
| EP | 3835258 | 6/2021 |
| WO | 2007/092844 | 8/2007 |
| WO | 2011/009919 | 1/2011 |
| WO | 2014/075850 | 5/2014 |
| WO | 2020/079403 | 4/2020 |

* cited by examiner

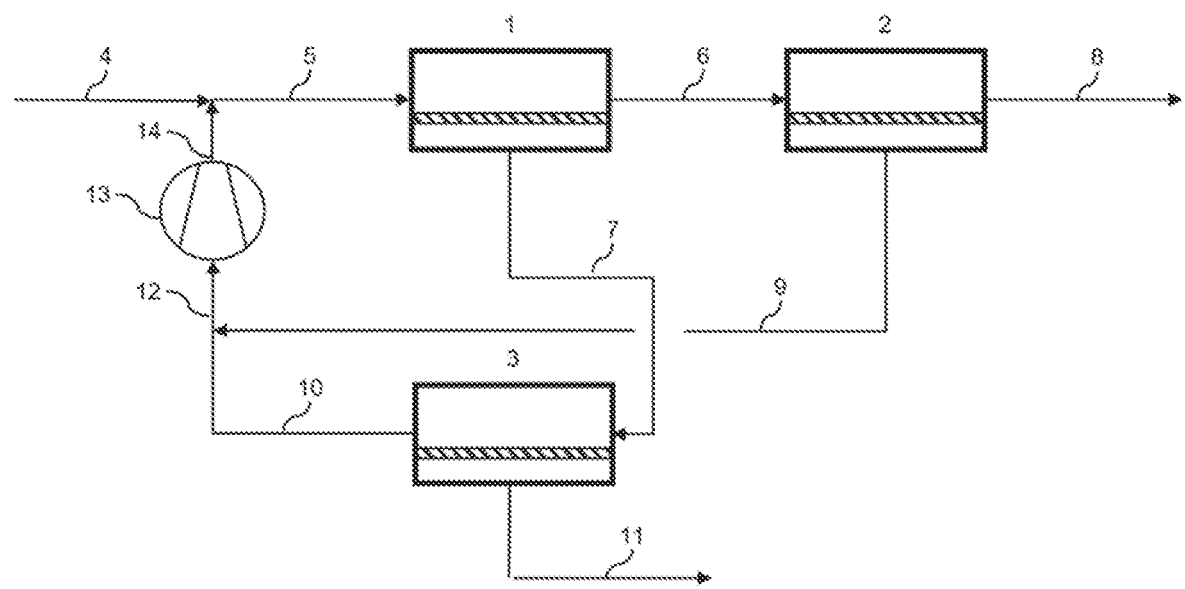

PROCESS FOR PRODUCING CARBON MONOXIDE-CONTAINING STREAMS

CROSS-REFERENCE TO RELATED APPLICATIONS

This application claims priority to European Application No. 21215852.1, filed on Dec. 20, 2021, the content of which is hereby incorporated by reference in its entirety.

BACKGROUND OF THE INVENTION

Field of the Invention

The present invention relates to a process for providing a carbon monoxide-containing stream. The process according to the invention is characterized by a separation of synthesis gas into a hydrogen-rich gas stream and a carbon monoxide-rich gas stream consisting of carbon monoxide to an extent of 85% by volume or more, wherein the separation is effected in an arrangement composed of at least three membrane separation stages. Prior to the performance of the membrane separation, the synthesis gas is pretreated for removal of secondary components present in the synthesis gas.

Description of Related Art

Processes for producing carbon monoxide-containing streams are known in the prior art. In the main, carbon monoxide is formed by the incomplete combustion of carbon-containing substances, for example coal gasification, carbon dioxide reforming or the partial oxidation of hydrocarbons. The problem here is that not only carbon monoxide but also other substances such as hydrogen are formed. A known process for producing carbon monoxide-containing streams having small proportions of hydrogen is the Otto process, but this is barely usable in industrial scale plants.

In this respect, what are obtained are typically gas mixtures that contain different proportions of carbon monoxide depending on the production process. If, however, a carbon monoxide-containing stream that has a high proportion of carbon monoxide and is therefore comparatively pure is to be obtained, a further separation of the gas mixture obtained is required. An example of a known process for separating gas mixtures is cryogenic fractionation into the individual substances. A corresponding process is described, for example, in DE 699 09 143 T2, where the cryogenic separation of synthesis gas is disclosed.

However, cryogenic fractionation is quite a costly and comparatively complex process because very cold methane streams have to be present and used for the absorption of CO and/or separation at very low temperatures is required, for example by means of cryogenic rectification. There is thus a need for a simple and comparatively inexpensive process for separating gas mixtures such as synthesis gas.

SUMMARY OF THE INVENTION

It was accordingly an object of the present invention to provide a process with which a carbon monoxide-containing stream can be produced in a simple and very inexpensive manner. The carbon monoxide-containing stream here should be of maximum purity, and the process should be notable if at all possible for high yields of carbon monoxide, i.e. only small losses of carbon monoxide during the separation process.

The object was achieved by the process according to the invention as described below. Preferred configurations are also specified below. The process according to the invention is a process for separating synthesis gas into a hydrogen-rich gas stream and a carbon monoxide-rich gas stream in a membrane separation unit comprising at least three membrane separation stages, wherein the ratio of hydrogen to carbon monoxide in the synthesis gas is in the range from 70:30 to 30:70, based on the respective proportion by volume of hydrogen and carbon monoxide in the synthesis gas, and wherein the process has the following steps:

a. providing synthesis gas and pretreating the synthesis gas for at least partial removal of one or more secondary component(s) present in the synthesis gas;
b. feeding a feed stream comprising the pretreated synthesis gas and a recyclate stream to the first separation stage to obtain a first retentate and a first permeate, wherein carbon monoxide is enriched in the first retentate and hydrogen in the first permeate;
c. feeding the first retentate to the second separation stage to obtain a second retentate and a second permeate, wherein the second retentate is withdrawn as carbon monoxide-rich gas stream and consists of carbon monoxide to an extent of 85% by volume or more, and wherein the second permeate is recycled upstream of the first separation stage;
d. feeding the first permeate to the third separation stage to obtain a third retentate and a third permeate, wherein the third permeate is withdrawn as hydrogen-rich gas stream and consists of hydrogen to an extent of 70% by volume or more, and wherein the third retentate is recycled upstream of the first separation stage,
wherein the second permeate and the third retentate are combined to form a single recyclate stream and the pressure of the recyclate stream is increased with the aid of a compressor before the recyclate stream is combined with the pretreated synthesis gas upstream of the first separation stage to give the feed stream used in step b), wherein the ratio of pretreated synthesis gas to recyclate stream in the feed stream is in the range of 4:1 to 1:1.5, preferably 3:1 to 1:1.2, more preferably 2.5:1 to 1:1, based on the respective standard volume flow rate of pretreated synthesis gas and recyclate stream.

The invention also includes the following embodiments:
1. Process for separating synthesis gas into a hydrogen-rich gas stream and a carbon monoxide-rich gas stream in a membrane separation unit comprising at least three membrane separation stages, wherein the ratio of hydrogen to carbon monoxide in the synthesis gas is in the range from 70:30 to 30:70, based on the respective proportion by volume of hydrogen and carbon monoxide in the synthesis gas, and wherein the process has the following steps:
   a. providing synthesis gas and pretreating the synthesis gas for at least partial removal of one or more secondary component(s) present in the synthesis gas;
   b. feeding a feed stream comprising the pretreated synthesis gas and a recyclate stream to the first separation stage to obtain a first retentate and a first permeate, wherein carbon monoxide is enriched in the first retentate and hydrogen in the first permeate;
   c. feeding the first retentate to the second separation stage to obtain a second retentate and a second permeate, wherein the second retentate is withdrawn as carbon monoxide-rich gas stream and consists of carbon monoxide to an extent of 85% by volume or more, and wherein the second permeate is recycled upstream of the first separation stage;

d. feeding the first permeate to the third separation stage to obtain a third retentate and a third permeate, wherein the third permeate is withdrawn as hydrogen-rich gas stream and consists of hydrogen to an extent of 70% by volume or more, and wherein the third retentate is recycled upstream of the first separation stage, wherein the second permeate and the third retentate are combined to form a single recycle stream and the pressure of the recycle stream is increased with the aid of a compressor before the recycle stream is combined with the pretreated synthesis gas upstream of the first separation stage to give the feed stream used in step b), wherein the ratio of pretreated synthesis gas to recycle stream in the feed stream is in the range of 4:1 to 1:1.5, preferably 3:1 to 1:1.2, more preferably 2.5:1 to 1:1, based on the respective standard volume flow rate of pretreated synthesis gas and recycle stream.

2. Process according to embodiment 1, wherein the second retentate consists of carbon monoxide to an extent of 87% by volume or more, preferably to an extent of 91% by volume, more preferably to an extent of 95% by volume or more.

3. Process according to embodiment 1 or 2, wherein the second retentate contains not more than 2% by volume, preferably not more than 1% by volume, of hydrogen.

4. Process according to any of the preceding embodiments, wherein the third permeate, depending on the composition of the synthesis gas, as well as the hydrogen, consists of further gaseous substances such as carbon dioxide, carbon monoxide.

5. Process according to embodiment 4, wherein the third permeate contains less than 3% by volume, preferably less than 2% by volume, more preferably less than 1% by volume, of carbon monoxide.

6. Process according to any of the preceding embodiments, wherein the second separation stage or the third separation stage, preferably the second separation stage, has the highest capacity.

7. Process according to any or the preceding embodiments, wherein the permeate-side pressure of the first separation stage is between 2.5 and 30 bar, preferably at least between 3.0 and 26 bar, more preferably between at least 3.3 and 21 bar.

8. Process according to any of the preceding embodiments, wherein the retentate-side pressure of the first separation stage is at least 20 to 80 bar, preferably 25 to 65 bar, more preferably 30 to 45 bar.

9. Process according to any of the preceding embodiments, wherein the transmembrane pressure in the first separation stage is 9 to 75 bar, preferably 9 to 60 bar, more preferably 13 to 40 bar.

10. Process according to any of the preceding embodiments, wherein the permeate-side pressure of the second separation stage is between 2.0 and 30 bar, preferably at least between 2.5 and 26 bar, more preferably between at least 2.8 and 21 bar.

11. Process according to any of the preceding embodiments, wherein the temperature in all three separation stages of the process is from 15 to 100° C., preferably between 25 and 60° C.

12. Process according to any of the preceding embodiments, wherein the three separation stages each consist or one or more separation modules, wherein, when there are multiple separation modules, these separation modules are connected in parallel and/or series within a separation stage.

13. Process according to embodiment 12, wherein the separation modules have a pure substance selectivity at 25° C. for hydrogen/carbon monoxide in the region of at least 25, preferably at least 30, more preferably at least 40.

14. Process according to any of the preceding embodiments, wherein the membrane material used is a material selected from the group consisting of polyimides, polyamides, polysulfones, cellulose acetates and derivatives thereof, polyphenylene oxides, polysiloxanes, polymers having intrinsic microporosity, mixed matrix membranes, facilitated transport membranes, polyethylene oxides, polypropylene oxides, carbon membranes, zeolites and mixtures thereof.

15. Integrated process for alkoxycarbonylation of C2 to C20 hydrocarbons having at least one olefinic double bond with a carbon monoxide stream and with an alcohol in the presence of a homogeneous catalyst system in a reaction zone, wherein the second retentate provided in step b) of the process according to any of embodiments 1 to 14 is used as carbon monoxide stream.

BRIEF DESCRIPTION OF THE DRAWING

The FIGURE shows a preferred embodiment of the process according to the present invention.

DETAILED DESCRIPTION OF THE INVENTION

The process according to the invention is consequently notable for an at least three-stage membrane separation. Corresponding processes can in many cases also be integrated into existing plants in a simple manner, since corresponding apparatuses are relatively space-saving and of simple construction. Furthermore, the operation is inexpensive because it is possible to avoid energy-demanding process steps, for example use of very cold substances or substance mixtures.

The feedstock for the process according to the invention is typical synthesis gases, i.e. gas mixtures containing mainly carbon monoxide and hydrogen. Corresponding synthesis gases are typically available at chemical production sites. The synthesis gas provided in the present invention is preferably already provided with a pressure in the range from 20 to 80 bar. A process by which synthesis gas can be provided with such a pressure is oil gasification. It is preferable in accordance with the invention that the synthesis gas is not compressed further before the membrane separation. i.e. there is no compressor for the fresh feed of synthesis gas used. According to the invention, there is only one compressor in the recycle stream.

The ratio of hydrogen to carbon monoxide in the synthesis gas is in the range from 70:30 to 30:70, preferably 60:40 to 40:60, based in each case on the respective proportion by volume of hydrogen and carbon monoxide in the synthesis gas. But it is also possible to use synthesis gases in which the ratio of hydrogen to carbon monoxide is in the range from 55:45 to 45:55, based on the respective proportion by volume of hydrogen and carbon monoxide in the synthesis gas. Preferred synthesis gases contain at least 30% by volume of carbon monoxide, preferably at least 40% by volume of carbon monoxide. This means that it is also possible even with a comparatively small membrane area to achieve high purities in the second retentate, i.e. the carbon monoxide-rich gas stream.

Synthesis gases also contain certain amounts of secondary components. Secondary components in synthesis gases may, for example, be water, carbon dioxide, sulfur compounds such as $H_2S$ and COS, C2 or higher hydrocarbons, or the like. The synthesis gas should preferably contain not more than 25% by volume, preferably 20% by volume, more preferably less than 15% by volume, of secondary components, where a lower level of secondary components tends to lead to better separability and higher purity of the carbon monoxide-containing stream. It is further preferable when the $CO/CH_4$ ratio in the synthesis gas used is more than 10 mol/mol, preferably more than 20 mol/mol and more preferably at least 40 mol/mol. Particular secondary components should be at least partly removed from the synthesis gas prior to the membrane separation. For this purpose, according to the invention, the pretreatment in step a. is provided, in which one or more secondary components are at least partly removed. The pretreatment may consist of one or more separate steps. A known process for removal of impurities such as $CO_2$ and $H_2S$ from the crude synthesis gas is a counter current absorption with a regenerative solvent, e.g. an alkanolamine-based chemical solvent (e.g. DIPA) or a hybrid solvent (chemical and physical solvents) such as mixtures of alkanolamine (e.g. DIPA) and sulfolane.

It is possible to use the process according to the invention to obtain very pure carbon monoxide-containing streams, which are also referred to in the context of the present invention as carbon monoxide-rich gas streams. Within the process described in this invention, these streams are obtained as the second retentate in the second separation stage and consist to an extent of at least 85% by volume or more of carbon monoxide. However, it is preferable when the second retentate, i.e. the carbon monoxide-rich gas stream, consists to an extent of at least 87% by volume or more of carbon monoxide, preferably to an extent of at least 91% by volume of carbon monoxide and more preferably to an extent of at least 95% by volume or more of carbon monoxide. It is also particularly preferable when the $H_2/CO$ ratio in the second retentate, i.e. in the carbon monoxide-rich gas stream, is less than 0.05 mol/mol.

Even if the aim of the present invention is to obtain a carbon monoxide-containing stream having high purity as the second retentate, it is barely possible by industrial means to produce a pure carbon monoxide stream. Depending on the end use for the carbon monoxide-containing stream obtained as the second retentate, there may not even be any need for a particularly high purity. However, it is at least preferable that only little hydrogen is present in the carbon monoxide-containing stream. The carbon monoxide-containing stream obtained as the second retentate preferably contains not more than 2% by volume of hydrogen, more preferably not more than 1% by volume of hydrogen.

It has already been mentioned that the core aim of the present invention is the provision of a carbon monoxide-containing stream as the second retentate, wherein the stream has a high purity, i.e. consists of carbon monoxide to an extent of at least 85% by volume or more. In the process according to the invention, however, the third permeate obtained is a hydrogen-rich gas stream consisting to an extent of 70% by volume or more of hydrogen. In particular, the purity of the hydrogen-rich gas stream obtained as the third permeate, in the context of the present invention, is less of a high priority than the purity of the second retentate. It is even preferable to attempt to obtain all the other gases present in the synthesis gas in the hydrogen-rich gas stream, especially and at least the carbon dioxide. Accordingly, the third permeate, depending on the composition of the synthesis gas, as well as the hydrogen, consists of further gaseous substances such as carbon dioxide.

The hydrogen-rich gas stream obtained as the third permeate may also contain small amounts of carbon monoxide. This may also be required in order to enhance the necessary separating action and to achieve a second retentate of maximum purity. However, a higher yield of carbon monoxide in the third permeate will be associated with a poorer yield. Thus, it is necessary to weigh up how the process is operated with reference to the respective composition of the synthesis gas. It is generally preferable in this aspect that the third permeate contains less than 3% by volume of carbon monoxide, preferably less than 2% by volume of carbon monoxide, more preferably less than 1% by volume of carbon monoxide.

The membrane separation by the process according to the invention is an at least three-stage process in which the stages are specifically connected to one another. The first separation stage is a membrane separation stage for separation of the feed stream to obtain a first retentate and a first permeate, wherein carbon monoxide is enriched in the first retentate and hydrogen in the first permeate. The second separation stage is a membrane separation stage that may be of identical or different construction compared to the first separation stage, for separation of the first retentate to obtain a second retentate and a second permeate. The third separation stage is a membrane separation stage that may be of identical or different construction compared to the first and second separation stages, for separation of the first permeate to obtain a third retentate and a third permeate. But it is also conceivable that the membrane separation is effected in four stages or more than four stages.

Membranes used in the individual membrane separation stages may be suitable gas separation membranes at which the synthesis gas can be separated on account of the different permeances for the individual gases in the mixture (=mass flow per unit time, unit area, pressure differential and layer thickness). The membrane material used in the gas separation membranes may be used, for example, in the form of hollow fibres or two-dimensional membranes. Preference is given to combining multiple gas separation membranes of this kind in one separation module. All three membrane separation stages may consist of one or more separation modules, wherein, when there are multiple separation modules, these separation modules are connected in parallel and/or series within a separation stage. The construction and number of separation modules may vary between the different membrane separation stages.

The apparatus of the invention and the process of the invention may in principle be implemented with any suitable membrane materials. Suitable membrane materials for the present process are those with which it is possible to separate synthesis gases into a hydrogen-rich gas stream and a carbon monoxide-rich gas stream. Membrane materials for the separation of mixtures of multiple substances may consist or multiple layers, for example in the case of composite membranes, or consist of a single material, for example in the case of integrally asymmetric membranes. The layer crucial for the actual separation is also referred to as separation-active layer, through which the hydrogen permeates more quickly than the carbon monoxide, which results in the desired separation. Membrane materials used for separation-active layer may especially be a material selected from the group consisting of polyimides, polyamides, polysulfones, cellulose acetates and derivatives thereof, polyphenylene oxides, polysiloxanes, polymers having intrinsic microporosity, mixed matrix membranes, facilitated transport membranes, polyethylene oxides, polypropylene oxides, carbon membranes, zeolites and mixtures thereof.

In a preferred embodiment of the present invention, a polyimide is used for the separation-active layer or for the complete membrane material. Suitable polyimide membranes are, for example, P84 polyimide and P84 HT polyimide from Evonik Fibres GmbH or mixtures of P84 polyimide and/or P84 HT polyimide with other membrane materials. A process for producing these membranes is disclosed in WO 2011/009919 A1, and it is possible to use any of the membrane materials disclosed therein in the process described here.

In the context of the present invention, the membrane materials are preferably used in the form of hollow fibre membranes and/or two-dimensional membranes. Further preferably, two or more of the hollow fibre membranes and/or two-dimensional membranes are assembled to form separation modules that are used in the three separation stages. Modules used may be any of the gas separation modules known in the art, for example hollow fibre modules, capillary modules, tubular modules, spiral-wound modules, cushion modules, plate modules or pocket modules.

The separation modules preferably have a pure substance selectivity at 25° C. for hydrogen/carbon monoxide of at least 25, further preferably of at least 30, more preferably of at least 40. Membranes of higher selectivity have the advantage that the separation becomes more effective and less second permeate has to be recycled from the second separation stage and/or less third retentate from the third separation stage. It should therefore be clear that the process according to the invention can be run in a much more economically viable manner in some cases with more selective membranes. Nevertheless, it is also possible to use less selective membranes, provided that it is possible to achieve the actual purpose, i.e. the provision of a carbon monoxide stream of maximum purity.

The separation stages of the present invention can also be defined in terms of their capacity. Capacity in the context of the present invention is understood to mean the separation capacity, which can be calculated from the membrane area per separation module and the number of separation modules per separation stage, multiplied by the hydrogen permeance of the membrane used. It is preferable in accordance with the invention that the second separation stage or third separation stage has the highest capacity. More preferably, the second separation stage has the highest capacity.

What is described as the driving force for the separation of the synthesis gas in the separation modules is a pressure differential between the retentate side and the permeate side, which is also referred to as transmembrane pressure, in the respective three separation stages. The pressure differential is based more particularly on the pressure of the feed stream being guided to the first separation stage. For this purpose, the feed stream may be compressed by means of a suitable compressor. In a preferred embodiment of the present invention, the pretreated synthesis gas and the feed stream, however, are not compressed but are already provided at the correct pressure. On the feed side, therefore, there is preferably no compressor. The process described in the present context, however, has a compressor for the recycle stream in order to bring the pressure of the recycle stream to the pressure of the pretreated synthesis gas before these are combined to give the feed stream to the first membrane separation stage. In order to generate the pressure differential, there may also be a vacuum pump on the permeate side of a separation stage, optionally also in addition to a compressor.

For the first separation stage, the pressure conditions are preferably as below. The pressure on the retentate side of the first separation stage, i.e. the pressure with which the feed stream is guided to the first separation stage, is preferably between 20 and 80 bar, further preferably between 25 and 65 bar, more preferably between 30 and 45 bar. The pressure on the permeate side of the first separation stage is preferably between 2.5 and 30 bar, further preferably between 3.0 and 26 bar, more preferably between 3.3 and 21 bar. This permeate-side pressure may be adjusted, for example, by means of a suitable pressure-reducing valve. It follows from this that the transmembrane pressure in the first separation stage is preferably between 9 and 75 bar, further preferably between 9 and 60 bar, more preferably between 13 and 40 bar. It will be apparent that the transmembrane pressure, as the pressure differential between retentate side and permeate side, can assume particular values only when there is a correspondingly high pressure on the retentate side or a correspondingly low pressure on the permeate side. The selection of suitable retentate pressures and permeate pressures for attainment of an industrially viable transmembrane pressure is familiar to the person skilled in the art. The unit bar here always means bar absolute (abbreviation: bara).

For the second separation stage, the pressure conditions are preferably as below. The pressure on the retentate side of the second separation stage, i.e. the pressure corresponding to the retentate side of the first separation stage with possible relatively small pressure drops, is preferably between 19.5 and 79.5 bar, further preferably between 24.5 and 64.5 bar, more preferably between 29.5 and 45 bar. The pressure on the permeate side of the second separation stage is preferably between 2.0 and 30 bar, further preferably between 2.5 and 26 bar, more preferably between 2.8 and 21 bar. This permeate-side pressure may be adjusted, for example, by means of a suitable pressure-reducing valve. It follows from this that the transmembrane pressure in the second separation stage is preferably between 9 and 75 bar, further preferably between 9 and 60 bar, more preferably between 13 and 40 bar. It will be apparent that the transmembrane pressure, as the pressure differential between retentate side and permeate side, can assume particular values only when there is a correspondingly high pressure on the retentate side or a correspondingly low pressure of the permeate side. The selection of suitable retentate pressures and permeate pressures for attainment of an industrially viable transmembrane pressure is familiar to the person skilled in the art. The unit bar here always means bar absolute (abbreviation: bara).

For the third separation stage, the pressure conditions are preferably as below. The pressure on the retentate side of the third separation stage, i.e. the pressure corresponding to the permeate side of the first separation stage with possible relatively small pressure drops, is preferably between 1.5 and 30 bar, further preferably between 2.0 and 26 bar, more preferably between 2.3 and 21 bar. The pressure on the permeate side of the third separation stage is preferably between 200 mbar and 10 bar, further preferably between 300 mbar and 8 bar, more preferably between 500 mbar and 5 bar. It follows from this that the transmembrane pressure in the third separation stage is preferably between 1.0 and 29.8 bar, further preferably between 1.0 and 25.8 bar, more preferably between 1.0 and 20.5 bar. It will be apparent that the transmembrane pressure, as the pressure differential between retentate side and permeate side, can assume particular values only when there is a correspondingly high pressure on the retentate side or a correspondingly low pressure on the permeate side. The selection of suitable retentate pressures and permeate pressures for attainment of an industrially viable transmembrane pressure is familiar to the person skilled in the art. The unit bar here always means bar absolute (abbreviation: bara).

According to the invention, the second permeate from the second separation stage and the third retentate from the third separation stage are combined to form a single recyclate stream and combined with the pretreated synthesis gas to give the feed stream. The pressure of the recyclate stream is increased with the aid of a compressor before combining it with the pretreated synthesis gas in order to bring the recyclate stream to the same pressure level. The ratio of pretreated synthesis gas to recyclate stream in the feed stream here is in the range from 4:1 to 1:5, preferably from 3:1 to 1:2, more preferably from 2.5:1 to 1:1, based in each case on the respective standard volume flow rate of pretreated synthesis gas and recyclate stream. It should be taken into account that the maximum or minimum possible ratio of pretreated gas to recyclate stream in the feed stream depends to a certain degree on the pure substance selectivity of the membrane modules used. The higher the pure substance selectivity, the smaller the amount of recyclate can be. However, corresponding dependences are known to the person skilled in the art or can be ascertained in quite a simple manner.

The process according to the invention can in principle take place at any suitable temperature in order thus to fulfil the purpose of the invention of providing a carbon monoxide stream of maximum purity. However, it is preferable that the temperature in all three separation stages of the process according to the invention is in the range from 15 to 100° C., more preferably between 25 and 60° C. The temperatures in the individual separation stages may be identical, but will in most cases differ on account of the gas expansion via the membrane without corresponding supply of heat. Depending on the temperature of the pretreated synthesis gas or of the feed stream and the desired temperature in the first separation stage, the feed stream may be heated or cooled before being fed into the first separation stage. In a preferred embodiment, the feed stream is heated before being fed into the first separation stage. The feed stream can be heated, for example, in a heat exchanger. Examples of heat carrier media that can be used are process steam or a suitable heat carrier oil. It is alternatively possible to heat the feed stream electrically.

According to the invention, the second retentate obtained in the process, i.e. the carbon monoxide-containing stream obtained, can be used for the chemical synthesis. Synthesis processes in which CO is required are known to the person skilled in the art. In a particularly preferred embodiment of the present invention, the second retentate is used in the alkoxycarbonylation. In alkoxycarbonylation, a hydrocarbon that has at least one multiple bond, preferably at least one olefinic double bond, is reacted with carbon monoxide and an alcohol to form the corresponding esters. In this respect, the present invention further provides an integrated process for alkoxycarbonylation of C2 to C20 hydrocarbons having at least one olefinic double bond with a carbon monoxide stream and with an alcohol in the presence of a homogeneous catalyst system in a reaction zone, wherein the second retentate provided in step b) of the process according to the invention is used as carbon monoxide stream.

In the alkoxycarbonylation in the integrated process of the present invention, preferably C3 to C16 hydrocarbons, more preferably C4 to C12 hydrocarbons, having at least one multiple bond, preferably at least one olefinic double bond, are used. Particularly preferred hydrocarbons used in the alkoxycarbonylation in the integrated process have only one olefinic double bond, in particular n-alkenes and isoalkenes having 2 to 20 carbon atoms, preferably 3 to 16 carbon atoms, more preferably 4 to 12 carbon atoms. The hydrocarbons used are preferably unsubstituted.

The alcohol used in the alkoxycarbonylation in the integrated process is a mono- or polyalcohol (two or more OH groups) having 1 to 15 carbon atoms, more preferably 1 to 10 carbon atoms, or a mixture of two or more mono- and/or polyalcohols. In a preferred embodiment, the polyalcohol is a diol, triol or tetraol, preferably a diol or triol, having the abovementioned number of carbon atoms. Suitable alcohols for the reaction in step a) are methanol, ethanol, 1-propanol, 1-butanol, 1-pentanol, 1-hexanol, 2-propanol, tert-butanol, 3-pentanol, 2-propylheptanol, cyclohexanol, phenol or mixtures thereof, preferably ethanol, 1-propanol, 1-butanol, 1-pentanol, 1-hexanol, 2-propanol, tert-butanol, 3-pentanol, 2-propylheptanol.

The alcohol used in the alkoxycarbonylation in the integrated process, when it is a monoalcohol, is used in a molar ratio to the hydrocarbon used (monoalcohol:hydrocarbon) of 2 to 20, preferably of 3 to 10 and more preferably of 4 to 6. The monoalcohol is thus added in a molar excess based on the hydrocarbon used. The alcohol may accordingly serve both as a reactant for the carbonylation and as solvent. The alcohol used in the alkoxycarbonylation in the integrated process, when it is a polyalcohol, is used in a molar ratio to the hydrocarbon used (hydrocarbon:polyalcohol) of 2 to 20, preferably of 3 to 10 and more preferably of 4 to 8. The polyalcohol is thus added in a molar deficiency based on the hydrocarbon used.

The alkoxycarbonylamino in the integrated process is performed in the presence of a homogeneous catalyst system. The homogeneous catalyst system preferably comprises at least one metal from group 8 to 10 of the periodic table of the elements (PTE) or a compound thereof, a phosphorus-containing ligand and an acid as co-catalyst.

The metal from groups 8 to 10 of the PTE is preferably palladium. The palladium is preferably used in the form of a precursor compound as a palladium compound coordinated by the phosphorus-containing ligand. Examples of palladium compounds that may be used as precursor compounds are palladium chloride [$PdCl_2$], palladium(II) acetylacetonate [$Pd(acac)_2$], palladium(II) acetate [$Pd(OAc)_2$], dichloro(1,5-cyclooctadiene)palladium(II) [$Pd(cod)Cl_2$], bis(dibenzylideneacetone)palladium(0) [$Pd(dba)_2$], tris(dibenzylideneacetone)dipalladium(0) [$Pd_2(dba)_3$] bis(acetonitrile)dichloropalladium(II) [$Pd(CH_3CN)_2C_2$], palladium (cinnamyl)dichloride [$Pd(cinnamyl)Cl_2$]. Preference is given to using the compounds [$Pd(acac)_2$] or [$Pd(OAc)_2$]. The concentration of palladium metal in the alkoxycarbonylation is preferably between 0.01 and 0.6 mol %, preferably between 0.03 and 0.3 mol %, more preferably between 0.04 and 0.2 mol %, based on the molar amount of the hydrocarbon used.

Suitable phosphorus-containing ligands of the catalyst system according to the invention preferably have a bidentate structure. Preferred phosphorus-containing ligands for the catalyst system according to the invention are benzene-based diphosphine compounds, as disclosed, for example, in EP 3 121 184 A2. The ligands may be combined with the palladium in a preliminary reaction so that the palladium-ligand complex is fed into the reaction zone or added to the reaction in situ and combined with the palladium there. The molar ratio of ligand:metal in the alkoxycarbonylation may be 1:1 to 10:1, preferably 2:1 to 6:1, more preferably 3:1 to 5:1.

The homogeneous catalyst system further comprises an acid, in particular a Brønsted or a Lewis acid. The Lewis acid used may, in particular, be aluminium triflate, aluminium chloride, aluminium hydride, trimethylaluminium, tris(pentafluorophenyl)borane, boron trifluoride, boron trichloride or mixtures thereof. Of the Lewis acids mentioned, preference is given to using aluminium triflate. The Lewis acid is preferably added in a molar ratio of Lewis acid:ligand of 1:1 to 20:1, preferably 2:1 to 15:1, more preferably 5:1 to 10:1.

Suitable Brønsted acids preferably have an acid strength pKa of ≤5, more preferably an acid strength pKa of ≤3. The stated acid strength pKa refers to the pKa determined under standard conditions (25° C., 1.01325 bar). For polyprotic acids, the acid strength pKa in the context of this invention relates to the pKa of the first protolysis step. The Brønsted acid is preferably added in a molar ratio of Brønsted acid:ligand of 1:1 to 15:1, preferably 2:1 to 10:1, more preferably 3:1 to 5:1.

The Brønsted acid used may in particular be perchloric acid, sulfuric acid, phosphoric acid, methylphosphonic acid or sulfonic acids. Examples of suitable sulfonic acids are methanesulfonic acid, trifluoromethanesulfonic acid, tert-butanesulfonic acid, p-toluenesulfonic acid (PTSA), 2-hydroxypropane-2-sulfonic acid, 2,4,6-trimethylbenzenesulfonic acid and dodecylsulfonic acid. Particularly preferred acids are sulfuric acid, methanesulfonic acid, trifluoromethanesulfonic acid and p-toluenesulfonic acid. The acid is preferably sulfuric acid. Carboxylic acids, on the other hand, are less suitable or not suitable at al.

The alkoxycarbonylation in the integrated process is preferably conducted at a temperature of 25 to 140° C., further preferably at a temperature of 80 to 120° C. and more preferably at a temperature of 90 to 110° C. The pressure in the alkoxycarbonylation may be between 5 and 60 bar, preferably between 10 and 40 bar, more preferably between 15 and 30 bar.

The alkoxycarbonylation in the integrated process takes place in a suitable reaction zone. The reaction zone for the reaction comprises at least one reactor, but may also consist of two or more reactors. The at least one reactor may in particular be selected from the group consisting of a stirred-tank reactor, a loop reactor, a jet-loop reactor, a bubble-column reactor or combinations thereof. If more than one reactor is used, the reactors may be identical or different.

The FIGURE of the present invention shows a preferred embodiment of the present invention. A pretreated synthesis gas (4) is combined therein with a recycle stream (14) and guided as feed stream (5) to the first membrane separation stage (1). The resultant first retentate (6) in which CO is enriched is guided to the second membrane separation stage (2) and subjected to a further membrane separation. The second retentate (8) obtained in the second membrane separation stage (2) is the carbon monoxide-rich gas stream, which is withdrawn and consists to an extent of 85% by volume or more of carbon monoxide. The first permeate (7) obtained in the first membrane separation stage (1) is guided to the third membrane separation stage (3). The third permeate (11) obtained in the third membrane separation stage (3) is the hydrogen-rich gas stream, which is withdrawn and consists to an extent of 70% by volume or more of hydrogen. The second permeate (9) obtained from the second membrane separation stage (2) and the third retentate obtained from the third membrane separation stage (3) are combined and compressed as common recyclate (12) by means of a compressor (13), before being combined with the pretreated synthesis gas (4).

The present invention is to be elucidated hereinafter by examples. These examples are specific embodiments that elucidate the invention, but should not be considered to be restrictive.

EXAMPLES

The examples that follow, in which synthesis gases have been separated in each case, were computer-assisted simulations. These simulated separation of the synthesis gases used in each case by a membrane separation unit having three membrane separation stages according to the FIGURE. The studies have been conducted in the Aspen Custom Modeler commercial simulation environment. The membrane model implemented therein is based on the known solution-diffusion model, which is used in the separation of gases by means of impervious polymeric membranes. The driving force is assumed to be the differential in partial pressure of the components between feed and permeate. The membrane model enables suitable discretization of a membrane module over the modelled length and assumes countercurrent flow. The temperatures in the three membrane separation stages in the simulation were each set to 40° C. The permeances for the individual membrane components can be taken from the respective examples.

Constant permeances were assumed. The influence of temperature on permeances and selectivity was neglected. Nor were non-ideal effects taken into account, for example pressure drop in the module, polarization of temperature and concentration, and the Joule-Thomson effect, because these effects do not have any significant effect on the general findings. In addition, the pretreatment in the simulation was not taken into account because it was possible to adjust the composition of the streams in the simulation as they would be established after a pretreatment.

Example 1: Separation of a Synthesis Gas ($H_2$:CO=about 50:50) at a Membrane with H2/CO Selectivity of 40

The simulation was effected as described above. The ratio of $H_2$ to CO in the synthesis gas used as feed was about 50:50 (cf. composition of the feed in Table 2). The synthesis gas is provided at a pressure of 40 bara (bara=bar absolute). The membrane used was a membrane having the customary permeances and selectivities that follow (cf. WO 2020/079403 A1).

TABLE 1

Overview of customary permeances and selectivities for particular gases

| Component | $H_2$ | CO | $N_2$ | $CH_4$ | $CO_2$ |
|---|---|---|---|---|---|
| Permeance [GPU*] | 200 | 5 | 4 | 2 | 50 |
| Selectivity [$H_2$/gas] | 1 | 40 | 50 | 100 | 4 | where 1 GPU = 1 × $10^{-6}$ $cm^3$(STP)/($cm^2$ · s · cmHg).

The first membrane separation stage is implemented with an area of 1063 $m^2$. The permeate pressure of the first separation stage is 6.3 bara, resulting in a transmembrane pressure of 33.7 bar in the 1st stage. The retentate from the first separation stage is processed with the second membrane separation stage. The membrane area of the second separation stage, at 3815 m², is larger than in the first separation stage. The permeate from the second separation stage is at a pressure of 6.3 bara. The transmembrane pressure is accordingly 33.7 bar. The permeate from the first separation stage is processed with the third membrane separation stage. The third membrane separation stage has an area of 2126 m². In this example, the second separation stage thus has the highest capacity. At a permeate pressure of 125 bara in the third separation stage, the resultant transmembrane pressure is 5 bar. The retentate from the third separation stage is combined with the permeate from the second separation stage to give the recyclate and brought by means of a compressor to a pressure of 40 bara. Subsequent, the recyclate is combined with the synthesis gas and sent to the first membrane separation stage. The standard volume flow rate of the synthesis gas in the present example is 10 000 m³ (STP)/h, and the standard volume flow rate of the recyclate is 5000 m³ (STP)/h. The result is thus a ratio of synthesis gas to recyclate stream of 2:1. What is obtained overall is a standard volume flow rate of the CO product (second retentate) of 5059 m³ (STP)/h. The CO yield of the membrane separation is 99.55%, and the CO product (second retentate) has a purity of 97.73%. The compositions of the individual streams are shown in Table 2.

TABLE 2

Composition of the respective streams in Example 1/the respective reference numerals from the Figure are given in brackets.

| Composition (mol %) | Feed (synthesis gas) (4) | CO product (second retentate) (8) | $H_2$ product (third permeate) (11) | Recyclate (14) |
|---|---|---|---|---|
| CO | 49.7% | 97.73% | 0.45% | 39.43% |
| $H_2$ | 49.6% | 1.0% | 99.4% | 59.7% |
| $N_2$ | 0.5% | 1.0% | 0.00% | 0.03% |
| $CH_4$ | 0.10% | 0.20% | 0.00% | 0.32% |
| $CO_2$ | 0.10% | 0.09% | 0.11% | 0.49% |

Example 2: Separation of a Synthesis Gas ($H_2$:CO=about 50:50) at a Membrane with $H_2$/CO Selectivity of 30

Example 2 was conducted very substantially like Example 1. Therefore, only the differences from Example 1 are noted hereinafter. In Example 2, by comparison with Example 1, a membrane having an $H_2$/CO selectivity of 30 was used. This is implemented by a reduction in the $H_2$ permeance from 200 to 150 GPU in the simulation. All other permeances are the same as in Table 1. The pretreated synthesis gas stream is also identical to Example 1. The membrane area in the first membrane separation stage is 1438 m², in the second membrane separation stage 4588 m², and in the third membrane separation stage 2877 m². In this example, the second separation stage thus has the highest capacity. The standard volume flow rate of the synthesis gas in the present example is 10 000 m³ (STP)/h, and the standard volume flow rate of the recyclate is 6000 m³ (STP)/h. The result is thus a ratio of synthesis gas to recyclate stream of 1.67:1. What is obtained overall is a standard volume flow rate of the CO product (second retentate) of 5047 m³ (STP)/h. The CO yield of the membrane separation is 99.35%, and the CO product (second retentate) has a purity of 97.76%. The compositions of the individual streams are shown in Table 3.

TABLE 3

Composition of the respective streams in Example 2/the respective reference numerals from the Figure are given in brackets.

| Composition (mol %) | Feed (synthesis gas) (4) | CO product (second retentate) (8) | $H_2$ product (third permeate) (11) | Recyclate (14) |
|---|---|---|---|---|
| CO | 49.7% | 97.76% | 0.66% | 39.73% |
| $H_2$ | 49.6% | 1.0% | 99.2% | 59.5% |
| $N_2$ | 0.5% | 1.0% | 0.00% | 0.03% |
| $CH_4$ | 0.10% | 0.20% | 0.00% | 0.32% |
| $CO_2$ | 0.10% | 0.06% | 0.14% | 0.42% |

Example 3: Separation of a Synthesis Gas ($H_2$:CO=about 50:50) at a Membrane with $H_2$/CO Selectivity of 25

Example 3 was conducted very substantially like Example 1. Therefore, only the differences from Example 1 are noted hereinafter. In Example 3, by comparison with Example 1, a membrane having an $H_2$/CO selectivity of 25 was used. This is implemented by a reduction in the $H_2$ permeance from 200 to 125 GPU in the simulation. All other permeances are the same as in Table 1. The pretreated synthesis gas stream is also identical to Example 1. The membrane area in the first membrane separation stage is 1729 m², in the second membrane separation stage 5239 m², and in the third membrane separation stage 3458 m². In this example, the second separation stage thus has the highest capacity. The standard volume flow rate of the synthesis gas in the present example is 10 000 m³ (STP)/h, and the standard volume flow rate of the recyclate is 7000 m³ (STP)/h. The result is thus a ratio of synthesis gas to recyclate stream of 1.43:1. What is obtained overall is a standard volume flow rate of the CO product (second retentate) of 5039 m³ (STP)/h. The CO yield of the membrane separation is 99.21%, and the CO product (second retentate) has a purity of 97.77%. The compositions of the individual streams are shown in Table 4.

TABLE 4

Composition of the respective streams in Example 3/the respective reference numerals from the Figure are given in brackets.

| Composition (mol %) | Feed (synthesis gas) (4) | CO product (second retentate) (8) | $H_2$ product (third permeate) (11) | Recyclate (14) |
|---|---|---|---|---|
| CO | 49.7% | 97.77% | 0.80% | 38.97% |
| $H_2$ | 49.6% | 1.0% | 99.0% | 60.3% |
| $N_2$ | 0.5% | 1.0% | 0.00% | 0.03% |
| $CH_4$ | 0.10% | 0.20% | 0.00% | 0.31% |
| $CO_2$ | 0.10% | 0.04% | 0.16% | 0.37% |

Example 4: Separation of a Synthesis Gas ($H_2$:CO=about 60:40) at a Membrane with $H_2$/CO Selectivity of 40

Example 4 was conducted very substantially like Example 1. Therefore, only the differences from Example 1 are noted hereinafter. The membrane area in the first membrane separation stage is 1268 in, in the second membrane separation stage 2901 m², and in the third membrane separation stage 2536 m². In this example, the second separation stage thus has the highest capacity. The standard volume flow rate of the synthesis gas in the present example is 10 000 m³ (STP)/h, and the standard volume flow rate of the recyclate is 4000 m³ (STP)/h. The result is thus a ratio of synthesis gas to recyclate stream of 2.5:1. What is obtained overall is a standard volume flow rate of the CO product (second retentate) of 4046 m³ (STP)/h. The CO yield of the membrane separation is 99.37%, and the CO product (second retentate) has a purity of 97.43%. The compositions of the individual streams are shown in Table 5.

TABLE 5

Composition of the respective streams in Example 4/the respective reference numerals from the Figure are given in brackets.

| Composition (mol %) | Feed (synthesis gas) (4) | CO product (second retentate) (8) | H₂ product (third permeate) (11) | Recyclate (14) |
|---|---|---|---|---|
| CO | 39.7% | 97.43% | 0.42% | 40.93% |
| H₂ | 59.6% | 1.0% | 99.5% | 58.1% |
| N₂ | 0.5% | 1.2% | 0.00% | 0.04% |
| CH₄ | 0.10% | 0.25% | 0.00% | 0.41% |
| CO₂ | 0.10% | 0.09% | 0.11% | 0.53% |

Example 5: Separation of a Synthesis Gas ($H_2$:CO=about 40:60) at a Membrane with $H_2$/CO Selectivity of 40

Example 5 was conducted very substantially like Example 1. Therefore, only the differences from Example 1 are noted hereinafter. The membrane area in the first membrane separation stage is 863 m², in the second membrane separation stage 4708 m², and in the third membrane separation stage 1727 m². In this example, the second separation stage thus has the highest capacity. The standard volume flow rate of the synthesis gas in the present example is 10 000 m³ (STP)/h, and the standard volume flow rate of the recyclate is 6000 m³ (STP)/h. The result is thus a ratio of synthesis gas to recyclate stream of 1.67:1. What is obtained overall is a standard volume flow rate of the CO product (second retentate) of 6072 m³ (STP)/h. The CO yield of the membrane separation is 99.68%, and the CO product (second retentate) has a purity of 97.93%. The compositions of the individual streams are shown in Table 6.

TABLE 6

Composition of the respective streams in Example 5/the respective reference numerals from the Figure are given in brackets.

| Composition (mol %) | Feed (synthesis gas) (4) | CO product (second retentate) (8) | H₂ product (third permeate) (11) | Recyclate (14) |
|---|---|---|---|---|
| CO | 59.7% | 97.93% | 0.51% | 38.30% |
| H₂ | 39.6% | 1.0% | 99.4% | 61.0% |
| N₂ | 0.5% | 0.8% | 0.00% | 0.03% |
| CH₄ | 0.10% | 0.16% | 0.00% | 0.26% |
| CO₂ | 0.10% | 0.09% | 0.12% | 0.46% |

Example 6: Separation of a Synthesis Gas ($H_2$:CO=about 50:50) at a Membrane with $H_2$/CO Selectivity of 40 and Lower Recirculation Example 6 was conducted very substantially like Example 1. Therefore, only the differences from Example 1 are noted hereinafter. The membrane area in the first membrane separation stage is 1615 m², in the second membrane separation stage 3201 M, and in the third membrane separation stage 3230 m². In this example, the third separation stage thus has the highest capacity. The standard volume flow rate of the synthesis gas in the present example is 10 000 m³ (STP)/h, and the standard volume flow rate of the recyclate is 3000 m³ (STP)/h. The result is thus a ratio of synthesis gas to recyclate stream of 3.33:1. What is obtained overall is a standard volume flow rate of the CO product (second retentate) of 4981 m³ (STP)/h. The CO yield of the membrane separation is 98.05%, and the CO product (second retentate) has a purity of 97.76%. The compositions of the individual streams are shown in Table 7.

TABLE 7

Composition of the respective streams in Example 6/the respective reference numerals from the Figure are given in brackets.

| Composition (mol %) | Feed (synthesis gas) (4) | CO product (second retentate) (8) | H₂ product (third permeate) (11) | Recyclate (14) |
|---|---|---|---|---|
| CO | 49.7% | 97.76% | 1.93% | 63.91% |
| H₂ | 49.6% | 1.0% | 97.9% | 35.2% |
| N₂ | 0.5% | 1.0% | 0.01% | 0.05% |
| CH₄ | 0.10% | 0.20% | 0.00% | 0.52% |
| CO₂ | 0.10% | 0.05% | 0.15% | 0.34% |

Comparing all the simulations with one another (see Table 8), it can be seen that very good results were achievable with different streams and different selectivities or the membranes. It was possible to obtain very pure carbon monoxide-containing gas streams as the second retentate. The CO yield was additionally very high in all cases.

TABLE 8

Overview of the experimental data and experimental results of all examples

| Example | $H_2$/CO selectivity | Ratio of $H_2$:CO | Ratio of synthesis gas:recyclate stream | Purity of second retentate (CO content) | CO yield |
|---|---|---|---|---|---|
| 1 | 40 | 50:50 | 2:1 | 97.73% | 99.55% |
| 2 | 30 | 50:50 | 1.67:1 | 97.76% | 99.35% |
| 3 | 25 | 50:50 | 1.43:1 | 97.77% | 99.21% |
| 4 | 40 | 60:40 | 2.5:1 | 97.43% | 99.37% |
| 5 | 40 | 40:60 | 1.67:1 | 97.93% | 99.66% |
| 6 | 40 | 50:50 | 3.33:1 | 97.76% | 98.05% |

The invention claimed is:

1. A process for separating synthesis gas into a hydrogen-rich gas stream and a carbon monoxide-rich gas stream in a membrane separation unit comprising at least three membrane separation stages, the process comprising:
   a. providing synthesis gas and pretreating the synthesis gas for at least partial removal of one or more secondary component(s) present in the synthesis gas, to obtain a pretreated synthesis gas;
   b. feeding a feed stream comprising the pretreated synthesis gas and a recyclate stream to a first separation stage to obtain a first retentate and a first permeate, wherein carbon monoxide is enriched in the first retentate and hydrogen is enriched in the first permeate;
   c. feeding the first retentate to a second separation stage to obtain a second retentate and a second permeate, wherein the second retentate is withdrawn as a carbon monoxide-rich gas stream and consists of carbon monoxide to an extent of 85% by volume or more, and wherein the second permeate is recycled upstream of the first separation stage; and d. feeding the first permeate to a third separation stage to obtain a third retentate and a third permeate, wherein the third permeate is withdrawn as a hydrogen-rich gas stream and consists of hydrogen to an extent of 70% by volume or more, and wherein the third retentate is recycled upstream of the first separation stage, wherein the second permeate and the third retentate are combined to form the single recycle stream and a pressure of the recycle stream is increased with the aid of a compressor before the recycle stream is combined with the pretreated synthesis gas upstream of the first separation stage to give the feed stream in b), wherein a ratio of the pretreated synthesis gas to the recycle stream in the feed stream is in a range of 4:1 to 1:1.5, based on a respective standard volume flow rate of the pretreated synthesis gas and the recycle stream, wherein a ratio of hydrogen to carbon monoxide in the synthesis gas is in a range from 70:30 to 30:70, based on a respective proportion by volume of hydrogen and carbon monoxide in the synthesis gas, and wherein the second separation stage or the third separation stage has the highest capacity of the at least three membrane separation stages, and wherein the synthesis gas has a $CO/CH_4$ ratio of more than 10 mol/mol.

2. The process according to claim 1, wherein the second retentate consists of carbon monoxide to an extent of 87% by volume or more.

3. The process according to claim 1, wherein the second retentate contains not more than 2% by volume of hydrogen.

4. The process according to claim 1, wherein the third permeate further comprises at least one further gaseous substance.

5. The process according to claim 4, wherein the third permeate contains less than 3% by volume of carbon monoxide.

6. The process according to claim 1, wherein a permeate-side pressure of the first separation stage is between 2.5 and 30 bar.

7. The process according to claim 1, wherein a retentate-side pressure of the first separation stage is at least 20 to 80 bar.

8. The process according to claim 1, wherein a transmembrane pressure in the first separation stage is 9 to 75 bar.

9. The process according to claim 1, wherein a permeate-side pressure of the second separation stage is between 2.0 and 30 bar.

10. The process according to claim 1, wherein a temperature in the first separation stage, the second separation stage, and the third separation stage of the process is from 15 to 100° C.

11. The process according to claim 1, wherein the first separation stage, the second separation stage, and the third separation stage each consist of one or more separation modules, wherein, when there are multiple separation modules in a single separation stage, the multiple separation modules are connected in parallel and/or series within the single separation stage.

12. The process according to claim 11, wherein the one or more separation modules have a pure substance selectivity at 25° C. for hydrogen/carbon monoxide of at least 25.

13. The process according to claim 1, wherein a membrane material of the at least three membrane separation stages is a material selected from the group consisting of polyimide, polyamide, polysulfone, cellulose acetate and a derivative thereof, polyphenylene oxide, polysiloxane, a polymer having intrinsic microporosity, a mixed matrix membrane, a facilitated transport membrane, polyethylene oxide, polypropylene oxide, a carbon membrane, zeolite, and a mixture thereof.

14. An integrated process, comprising:
reacting $C_2$ to $C_{20}$ hydrocarbons having at least one olefinic double bond in an alkoxycarbonylation with a carbon monoxide stream and with an alcohol in the presence of a homogeneous catalyst system in a reaction zone, wherein the carbon monoxide stream is the second retentate obtained in b) of the process according to claim 1.

15. The process according to claim 1, wherein the ratio of the pretreated synthesis gas to the recycle stream in the feed stream is in the range of 2.5:1 to 1:1.

16. The process according to claim 2, wherein the second retentate comprises carbon monoxide to an extent of 95% by volume or more.

17. The process according to claim 4, wherein the at least one further gaseous substance is carbon dioxide and/or carbon monoxide.

18. The process according to claim 1, wherein the second separation stage has the highest capacity.

19. The process according to claim 10, wherein the temperature in the first separation stage, the second separation stage, and the third separation stage is between 25 to 60° C.

20. The process according to claim 1, wherein the synthesis gas has at least 40% by volume of carbon monoxide and a $CO/CH_4$ ratio of more than 40 mol/mol.

* * * * *